United States Patent
Sliwa et al.

(10) Patent No.: US 11,801,082 B2
(45) Date of Patent: Oct. 31, 2023

(54) BALLOON-IN-BASKET ABLATION CATHETER

(71) Applicant: St. Jude Medical, Cardiology Division, Inc., St. Paul, MN (US)

(72) Inventors: John W. Sliwa, San Jose, CA (US); Stephen A. Morse, Menlo Park, CA (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 467 days.

(21) Appl. No.: 16/619,780

(22) PCT Filed: Jun. 5, 2018

(86) PCT No.: PCT/US2018/036140
§ 371 (c)(1),
(2) Date: Dec. 5, 2019

(87) PCT Pub. No.: WO2018/226751
PCT Pub. Date: Dec. 13, 2018

(65) Prior Publication Data
US 2020/0163707 A1 May 28, 2020

Related U.S. Application Data

(60) Provisional application No. 62/515,500, filed on Jun. 5, 2017.

(51) Int. Cl.
*A61B 18/14* (2006.01)
*A61B 18/02* (2006.01)
(Continued)

(52) U.S. Cl.
CPC .............. *A61B 18/02* (2013.01); *A61B 18/06* (2013.01); *A61B 18/082* (2013.01);
(Continued)

(58) Field of Classification Search
CPC ....... A61B 18/02; A61B 18/06; A61B 18/082; A61B 18/1492; A61B 2018/1497; A61B 18/20; A61B 2090/3966; A61B 2017/320069; A61B 2018/0022; A61B 2018/00214; A61B 2018/00226; A61B 2018/00232; A61B 2018/00238; A61B 2018/00267; A61B 2018/00375;
(Continued)

(56) References Cited

U.S. PATENT DOCUMENTS 6,142,993 A * 11/2000 Whayne ............. A61B 18/1492
606/41
9,867,556 B2 * 1/2018 Balachandran ...... A61B 5/6853
(Continued)

FOREIGN PATENT DOCUMENTS

WO 2018/226752 A1 12/2018

*Primary Examiner* — Aaron F Roane
(74) *Attorney, Agent, or Firm* — Armstrong Teasdale LLP

(57) ABSTRACT

A catheter comprises an expandable spline structure defining a distal tip portion of the catheter. The spline structure comprises a plurality of individual splines, and each spline is configured to support a plurality of energy transfer elements and/or temperature sensors. An expandable balloon configured to be associated with the spline structure is unattached to the spline structure along its length.

25 Claims, 9 Drawing Sheets

(51) Int. Cl.
*A61B 18/06* (2006.01)
*A61B 18/08* (2006.01)
*A61B 18/20* (2006.01)
*A61B 90/00* (2016.01)
*A61B 17/32* (2006.01)
*A61B 18/00* (2006.01)

(52) U.S. Cl.
CPC .......... *A61B 18/1492* (2013.01); *A61B 18/20* (2013.01); *A61B 2017/320069* (2017.08); *A61B 2018/0022* (2013.01); *A61B 2018/00267* (2013.01); *A61B 2018/00375* (2013.01); *A61B 2018/00577* (2013.01); *A61B 2018/00821* (2013.01); *A61B 2018/0212* (2013.01); *A61B 2090/3966* (2016.02); *A61B 2218/002* (2013.01)

(58) Field of Classification Search
CPC   A61B 2018/00577; A61B 2018/00821; A61B 2018/00791; A61B 2018/00797; A61B 2018/00803; A61B 2018/00809; A61B 2018/00815; A61B 2018/0212; A61B 2218/002

USPC .......................................................... 606/14
See application file for complete search history.

(56) References Cited

U.S. PATENT DOCUMENTS

| | | | |
|---|---|---|---|
| 2004/0082859 A1* | 4/2004 | Schaer | A61B 18/1492 600/459 |
| 2005/0015083 A1 | 1/2005 | Koblish et al. | |
| 2006/0085054 A1* | 4/2006 | Zikorus | A61B 18/08 607/113 |
| 2009/0299355 A1 | 12/2009 | Bencini et al. | |
| 2010/0168647 A1 | 7/2010 | Tegg et al. | |
| 2012/0143298 A1 | 6/2012 | Just et al. | |
| 2013/0197499 A1* | 8/2013 | Lalonde | A61B 18/02 606/21 |
| 2013/0197555 A1* | 8/2013 | Schaer | A61N 7/022 606/170 |
| 2015/0133760 A1 | 5/2015 | Kordis et al. | |
| 2016/0051321 A1* | 2/2016 | Salahieh | A61B 8/12 606/46 |
| 2017/0042614 A1* | 2/2017 | Salahieh | A61M 25/1011 |
| 2018/0325585 A1* | 11/2018 | Bar-Tal | A61B 5/6885 |
| 2019/0059818 A1* | 2/2019 | Herrera | A61B 18/1492 |

* cited by examiner

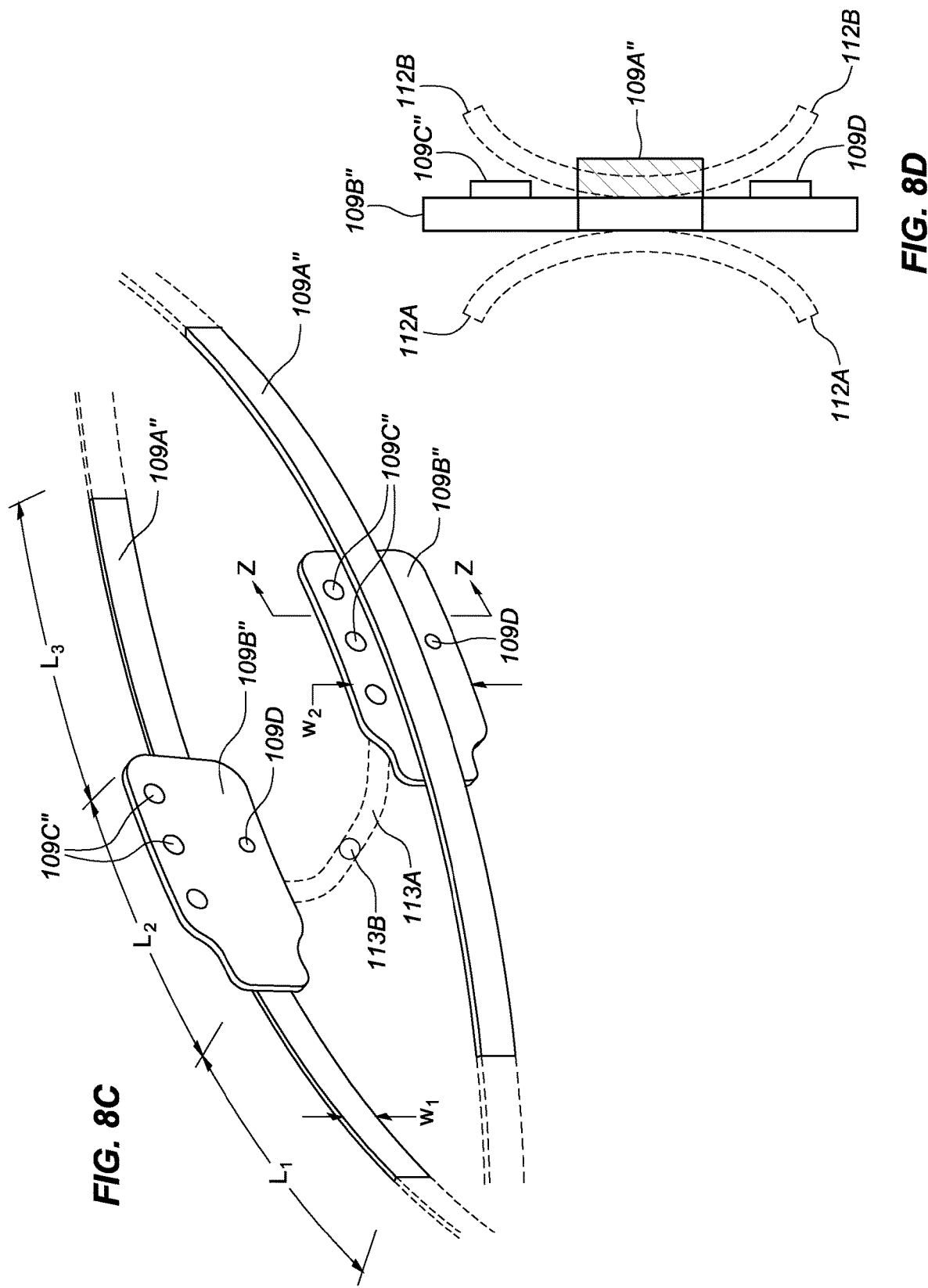

BALLOON-IN-BASKET ABLATION CATHETER

CROSS-REFERENCE TO RELATED APPLICATIONS

This application is a National Stage Entry of International application no. PCT/US2018/036140, filed 5 Jun. 2018 (the '140 application), and published under International publication no. WO 2018/226751 on 13 Dec. 2018. This application claims priority to Provisional patent application No. 62/515,500, filed 5 Jun. 2017 (the '500 application). The '140 application and the '500 application are all hereby incorporated by reference as though fully set forth herein.

BACKGROUND a. Field

This disclosure relates to a combination balloon-basket catheter for electrical mapping and tissue ablation.

b. Background Art

Electrophysiology (EP) catheters are used in a variety of diagnostic and/or therapeutic medical procedures to correct conditions such as atrial arrhythmia, including for example, ectopic atrial tachycardia, atrial fibrillation, and atrial flutter. Arrhythmia can create a variety of dangerous conditions including irregular heart rates, loss of synchronous atrioventricular contractions and stasis of blood flow which can lead to a variety of ailments and even death.

Typically in a procedure, a catheter is manipulated through a patient's vasculature to, for example, a patient's heart, and carries one or more electrodes which may be used for mapping, ablation, diagnosis, or other treatments. Once at the intended site, treatment may include radio frequency (RF) ablation, cryoablation, lasers, chemicals, high-intensity focused ultrasound, etc. An ablation catheter imparts such ablative energy to cardiac tissue to create a lesion in the cardiac tissue. This lesion disrupts undesirable electrical pathways and thereby limits or prevents stray electrical signals that lead to arrhythmias. As readily apparent, such treatment requires precise control of the catheter during manipulation to and at the treatment site, which can invariably be a function of a user's skill level.

Prior practice for delivering multiple ablations to tissue involves making a first ablation at a single point with an ablation catheter, then moving the ablation catheter on to the second ablation at a second point, and then moving to ablation catheter to the third site and so on. The single point ablations are made, often adjacent to one another, creating a lesion line. A frequent location for ablation lines are around/between the pulmonary veins in the left atrium of the heart. There are devices in development or being commercialized that attempt to achieve a sufficient block of ablations with minimal applications of energy. These are typically referred to as "one-shot-PVI" (pulmonary vein isolation) devices. Existing designs include diagnostic catheters with a hoop and balloon mounted designs with features to apply energy. Existing designs are challenged when it comes to maintaining consistent contact between the tissue/vessel and all of the electrodes.

BRIEF SUMMARY

In an embodiment, a catheter comprises an expandable spline structure defining a distal tip portion of the catheter, the spline structure comprising a plurality of individual splines, each spline configured to support a plurality of energy transfer elements; and an expandable balloon configured to be positioned inside the spline structure; wherein the balloon and the spline structure are unattached along a length of the spline structure.

In another embodiment, a catheter comprises an expandable spline structure defining a distal tip portion of the catheter, the spline structure comprising a plurality of individual splines, each spline configured to support a flexible circuit including at least one of an energy transfer element and a temperature sensor; and an expandable balloon configured to be positioned inside the spline structure.

In another embodiment, a catheter comprises an expandable spline structure defining a distal tip portion of the catheter, the spline structure comprising a plurality of individual splines, each spline configured to support a plurality of energy transfer elements; and an expandable first balloon configured to be positioned inside the spline structure; wherein the first balloon is uninflated upon entry into the spline structure.

BRIEF DESCRIPTION OF THE DRAWINGS

FIG. 8C is a schematic view of two adjacent splines in accordance with the present disclosure.

FIG. 8D is an isometric cross-sectional view through line Z-Z of FIG. 8C, in accordance with the present disclosure.

DETAILED DESCRIPTION

Figure 1:
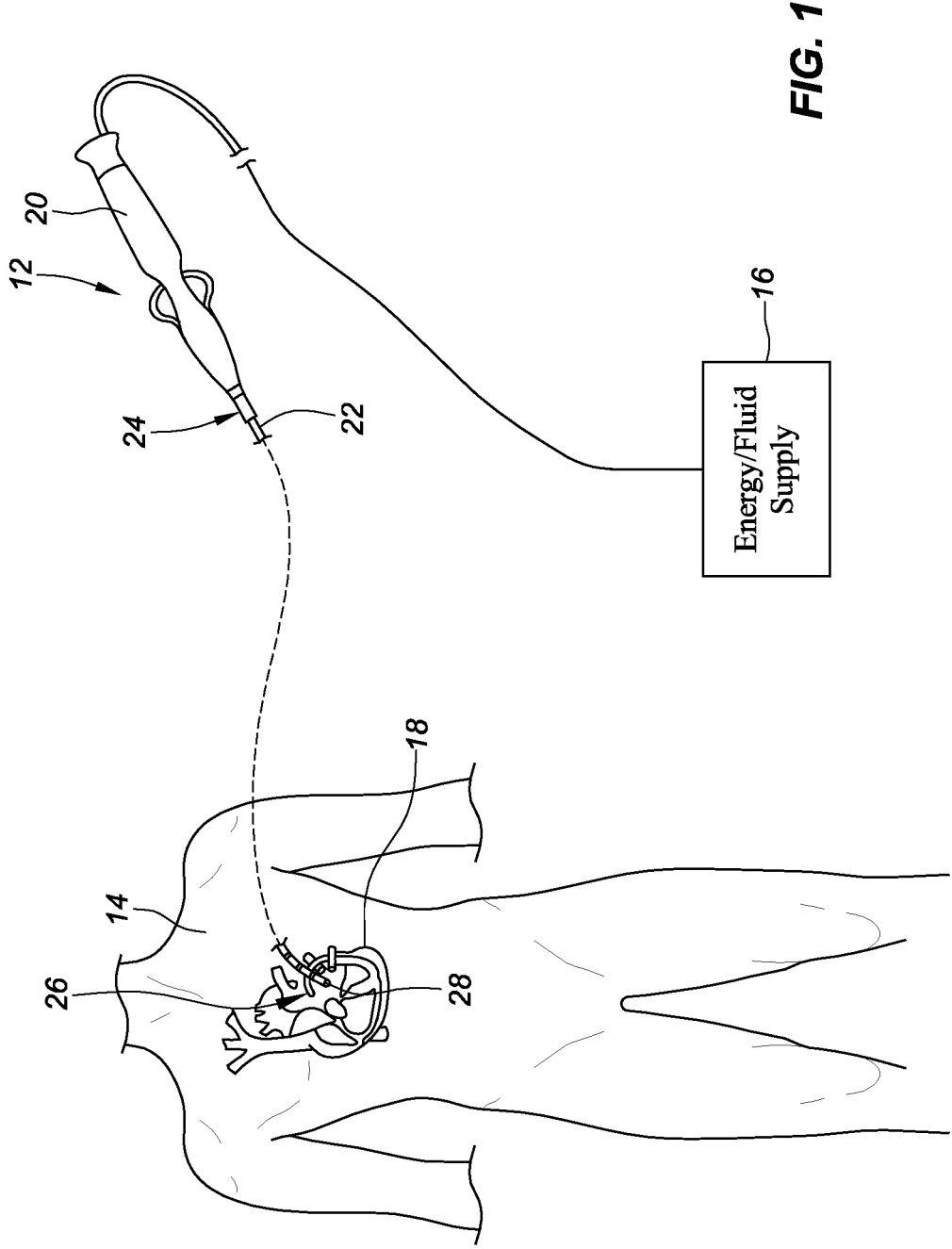
FIG. 1 is a schematic view depicting an embodiment of a catheter in accordance with the present disclosure.

FIG. 1 is a schematic view depicting a catheter 12 for use in a patient's body 14 and connected to an energy/fluid supply 16 (e.g., a radiofrequency (RF) ablation generator, a coolant supply) according to the present disclosure. In an embodiment, the catheter 12 may be an ablation catheter. The catheter 12 can be configured to be inserted into the patient's heart 18. The catheter 12 may include a handle 20 and a shaft 22 having a proximal end portion 24, a distal end portion 26, and a tip portion 28 disposed at the distal end portion 26 of the shaft 22. The catheter 12 may further include other conventional components such as, for example and without limitation, a temperature sensor, a position sensor, additional sensors or electrodes, and corresponding conductors or leads.

The shaft 22 can be an elongate, tubular, flexible member configured for movement within the body 14. The tip portion 28 of the shaft 22 supports, for example and without limitation, sensors and/or electrodes mounted thereon. The tip portion 28 may include ablation elements (e.g., ablation tip electrodes for delivering RF ablative energy). The shaft 22 may also permit transport, delivery, and/or removal of fluids (including irrigation fluids, cryogenic ablation fluids, and bodily fluids), medicines, and/or surgical tools or instruments.

Figure 2:
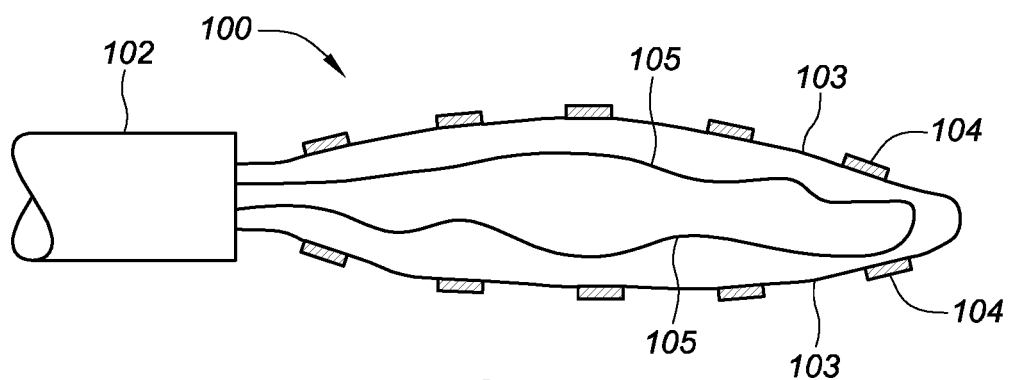
FIG. 2 is a schematic view of an embodiment of a balloon-in-basket device in accordance with the present disclosure.

FIG. 2 is a schematic view of a balloon-in-basket device 100 forming the distal tip portion of an ablation catheter, such as the catheter 12 described above with respect to FIG. 1. The illustrated embodiment includes a delivery lumen (or port) 102, a spline structure 103 supporting multiple energy transfer elements 104, and an interior inflatable ablating balloon 105. The balloon 105 is deflated and the basket splines 103 are collapsed such that the device 100 is deliverable through a bodily lumen to an ablation site.

The energy transfer elements 104 can include, for example, but not limited to, electrodes, flexible electrodes, ultrasound transducers, lasers, chemical ablation sources, cryoablation sources, and/or heat ablation sources. The energy transfer elements 104 can also include ablation elements, such as those described in commonly owned U.S. Provisional Patent Application No. 62/515,501 which is hereby incorporated by reference in its entirety as though fully set forth herein.

The spline structure 103 can be made from a material that retains its shape and permits self-expansion after being collapsed, such as nitinol or other materials that have shape memory or superelasticity. The energy transfer elements 104 situated along the spline structure 103 can be flexible electrodes used to characterize and map tissue that they come into contact with at a treatment site. In an embodiment, the treatment site can be the tissue forming and surrounding the pulmonary veins, a frequent origination site for the abnormal electrical activity that results in atrial fibrillation. In other embodiments, the treatment site can be renal artery tissue or a bodily ostium, lumen, or sphincter. Following delivery to the treatment site, such as through delivery lumen 102, the spline structure 103 can mechanically expand such that the energy transfer elements 104 preferably abut potential pulmonary vein target tissue. This expansion of the spline structure 103 is schematically illustrated in FIG. 3.

In addition, the balloon 105 can expand, such as when cryogenic fluid or heated fluid (e.g., saline) is delivered to the internal chamber of the balloon 105 via delivery lumen 102. The expanded balloon 105, shown schematically in FIG. 4, can allow for cryogenic or thermal ablation of target tissue abutting the pulmonary veins.

Figure 3:
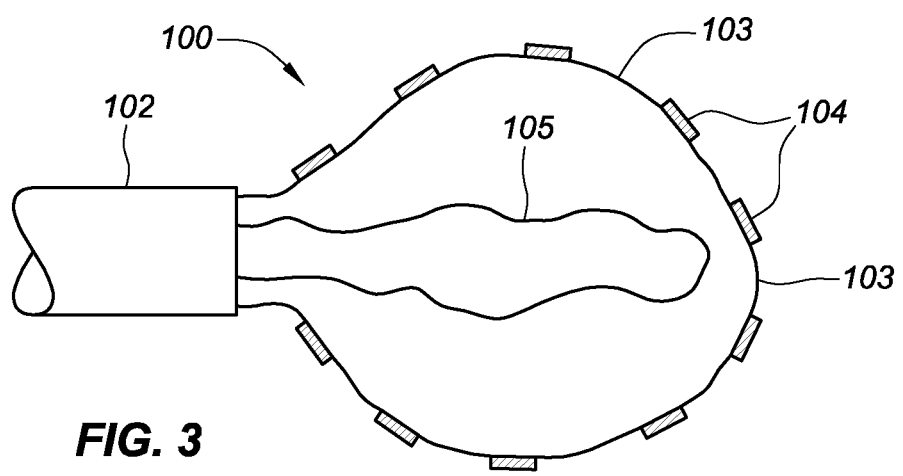
FIG. 3 is a schematic view of an embodiment of a balloon-in-basket device in accordance with the present disclosure.
Figure 4:
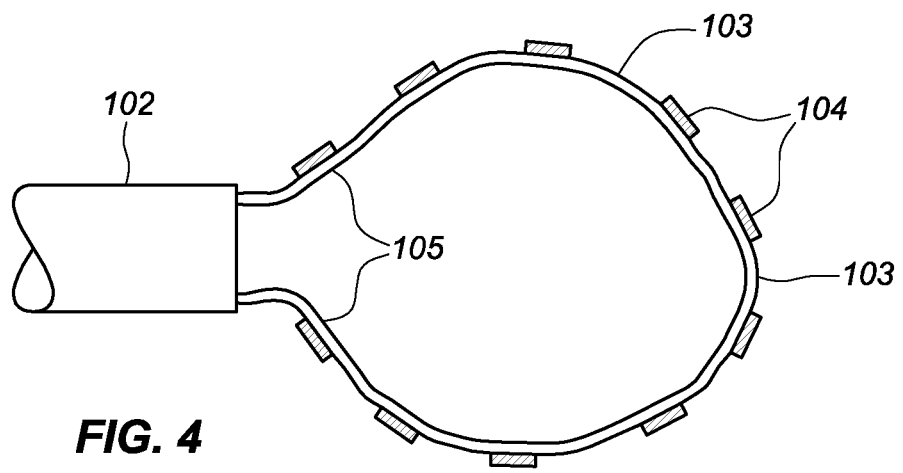
FIG. 4 is a schematic view of an embodiment of a balloon-in-basket device in accordance with the present disclosure.

It should be noted that the balloon 105 and the spline structure 103 can be structurally separate, as illustrated in FIGS. 2-4. In other words, the balloon 105 and the spline structure 103 are not bonded, laminated, integrated, or otherwise attached to each other. This structural separation allows the balloon 105 and the spline structure 103 to be separately expandable/collapsible, as well as separately introducible.

Several embodiments of the combined spline structure 103 and balloon 105 exist in accordance with the present invention. For example, the spline structure 103 can mechanically engage tissue (e.g., pulmonary vein tissue) and support energy transfer elements 104 (e.g., ablating RF electrodes) while the balloon 105 is separately inflated against the tissue and spline structure 103, as in FIG. 4. Cryogenic or heated fluid can flow through the inflated balloon 105. The energy transfer elements 104 can also be used for mapping or pacing cardiac tissue.

In another example, the energy transfer elements 104 can be used for only mapping or pacing, and not for ablation. In this case, the inflated balloon 105 can ablate tissue using cryogenic fluid or hot saline, for example.

In another example, the inflated balloon 105 can serve the purpose of causing the spline structure 103 to directly abut the target tissue, such that the spline energy transfer elements 104 can perform RF ablation on the tissue. The inflated balloon 105 may allow the splines to attain a more favorable shape for close tissue contact than would be possible via mechanical actuation of the spline structure alone (i.e., without the balloon 105). In this example, the energy transfer elements 104 may also map or pace tissue.

In another example, the energy transfer elements 104 on the spline structure 103 can perform ablation (regardless of how they are actuated against the tissue), and the inflated balloon 5 can serve the primary purpose of inhibiting blood flow from the pulmonary veins into the spline structure 103.

Figure 5A:
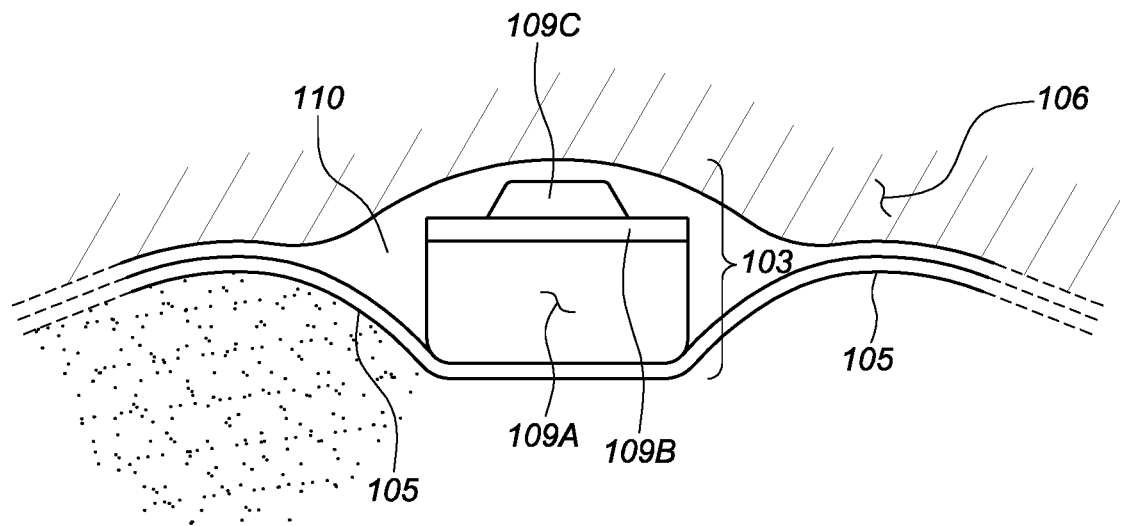
FIG. 5A is a schematic view of an embodiment associated with potential axial blood leakage.

FIG. 5A schematically illustrates an embodiment associated with potential axial blood leakage. When the spline structure 103 and the balloon 105 are in their expanded state abutting target tissue 106, blood can leak along the spline structure 103 into a triangular open channel area 110 defined by the target tissue 106, the balloon 105, and a flexible electrode 109C (or another energy transfer element as described above) sitting on top of a flexible circuit 109B, which in turn sits on top of a metal spline core 109A of the spline structure 103. The blood leakage into the open channel area 110 can reduce the thermal effect (whether cooling or heating) of ablation.

Figure 5B:
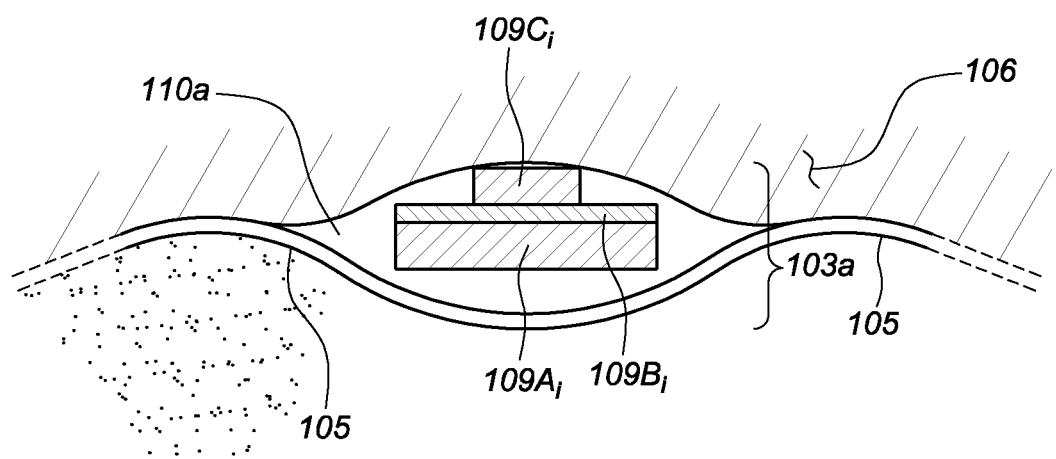
FIG. 5B is a schematic view depicting solutions to the potential axial blood leakage illustrated in FIG. 5A, in accordance with the present disclosure.

FIG. 5B is a schematic view depicting solutions to the axial blood leakage illustrated in FIG. 5A. FIG. 5B shows a spline structure 103a (including a metal spline core 109A$_i$, a flexible circuit 109B$_i$, and a flexible electrode 109C$_i$) with a modified cross-sectional shape that leaves a reduced open channel area 110a into which blood can leak. The spline structure 103a can be further modified to include an added material, such as elastomeric silicone or urethane (not shown), which can be placed in or near the reduced open channel area 110a in order to create a better blood-sealing fit.

Alternatively or additionally, a gel or compliant coating (not shown) can be employed on the surface of the balloon 105 or spline structure 103 to afford such a seal against blood leakage. The gel or compliant coating can be configured to withstand hot or cold ablation temperatures, to be resistant to shedding, and to be compatible with blood. The gel or compliant coating could be applied to the balloon 105 or the spline structure 103 during manufacturing, or it could be applied by a user. Alternatively, the balloon 105 could extrude the gel or compliant coating out of small holes in the balloon wall (not shown) in order to fill gaps between the balloon 105 and the tissue 106.

Figure 6:
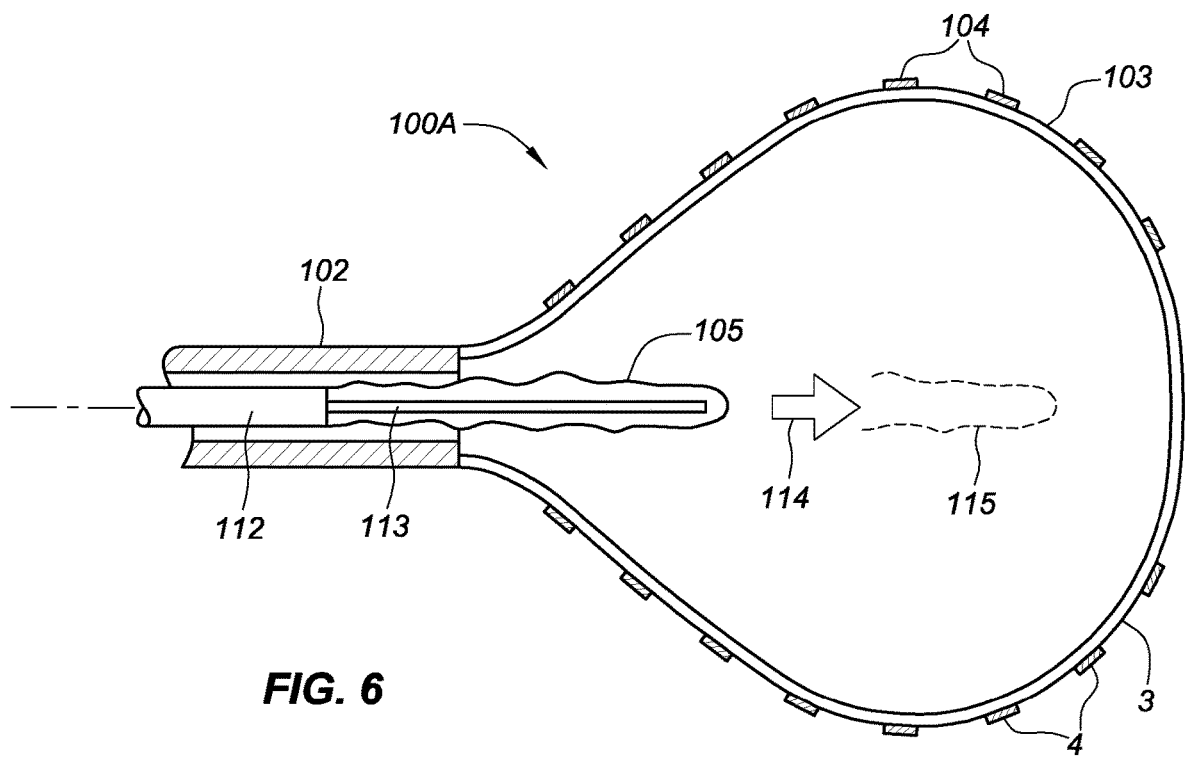
FIG. 6 is a schematic view of another embodiment of a balloon-in-basket device in accordance with the present disclosure.

FIG. 6 is a schematic illustration of another embodiment of a balloon-in-basket device 100A with the spline structure 103 mechanically expanded to about 75% of maximum expansion. In this embodiment, the balloon 105, shown here in its uninflated state, is mounted on a catheter, wire, or shaft 112 that has been inserted through a working port in lumen 102. The uninflated balloon 105 can be pushed forward as indicated by arrow 114 to assume position 115 where it can then be inflated. Thus, the device 100A can be used can be used in a non-obstructing manner (i.e., when the balloon 105 is not inflated, fluid can flow around it) or in an obstructing manner (i.e., when the balloon 105 is inflated).

In an another embodiment, the balloon 105 can be pre-assembled in the spline structure 103 and an inflating lumen 113 for the balloon 105 can be later inserted and flow-coupled in-situ to the balloon 105. The advantage of such an embodiment is that the balloon 105 can be larger or thicker-walled than it would otherwise need to be in order to fit through a working port.

Figure 7:
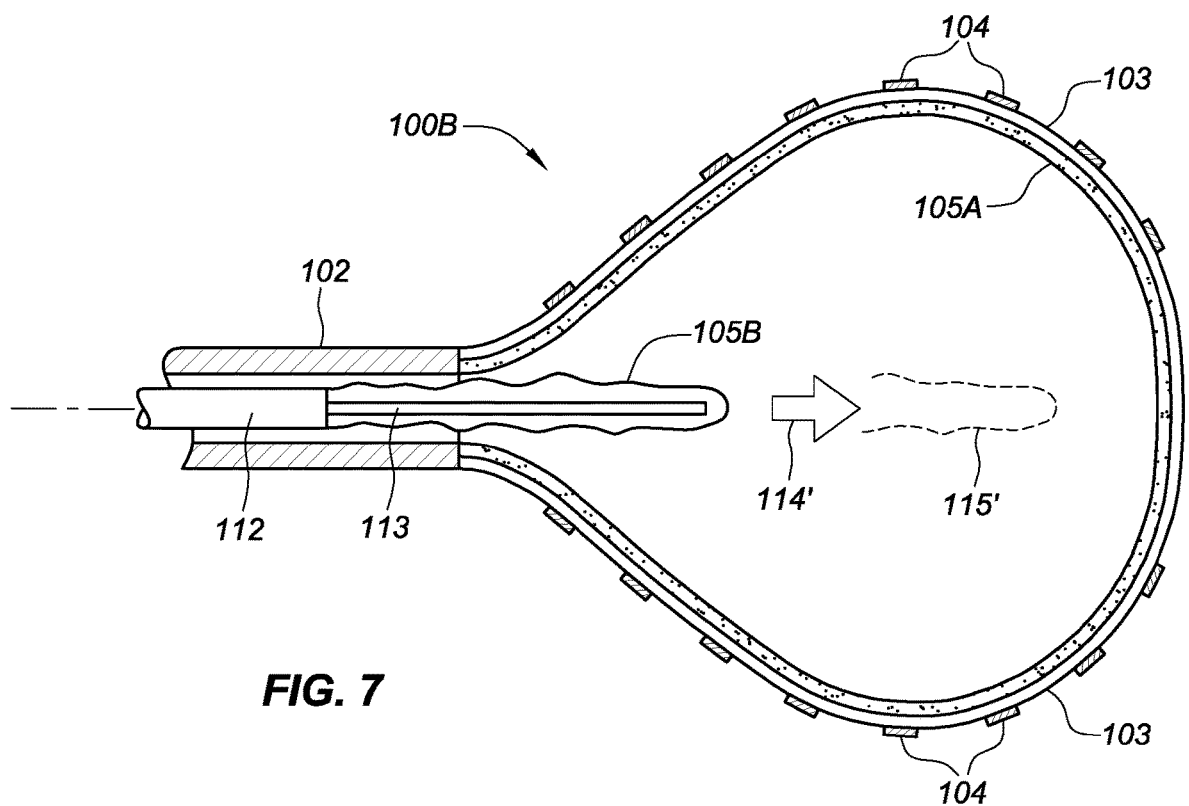
FIG. 7 is a schematic view of another embodiment of a balloon-in-basket device in accordance with the present disclosure.

FIG. 7 schematically depicts another embodiment a balloon-in-basket device 100B in which there is more than one balloon. Double balloons have been used to prevent cryo-coolant from leaking into blood upon the failure of one of the balloons. The two balloons, 105A and 105B, shown in FIG. 7 are not coinflated. The outer balloon 105A is inflated to anchor the spline structure 103. The inner balloon 105B is inflated against the tissue and already deployed outer balloon 105A to perform thermal ablation (either cooling or heating). The outer balloon 105A not only acts as a backup in case of failure of the inner balloon 105B, but it also functions as an independent fixation means for the spline structure 103. The outer balloon 105A can be inflated, if desired, by a non-coolant gas or liquid, such as carbon dioxide or saline. The inner balloon 105B is shown as being inserted into the interior of the spline structure 103 in the direction of arrow 114' to position 115' before inflation. A working port arrangement is not necessarily required for this embodiment, as the two balloons, 105A and 105B, and the spline structure 103 can all be part of the same device 100B. After cryoablation or hot fluid ablation, the gas or liquid in inner balloon 105B can be deflated while the outer balloon 105A remains inflated to fixate the spline structure 103 in a way that prevents tissue cooling.

Figure 8A:
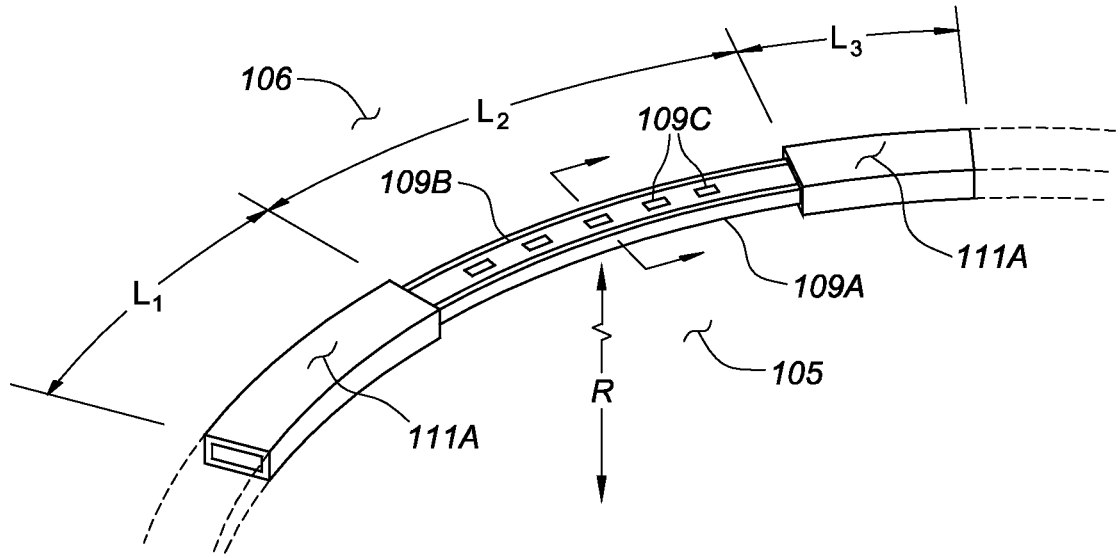
FIG. 8A is a schematic perspective and side view of a single-basket spline subassembly in accordance with the present disclosure.

FIG. 8A depicts schematic perspective and side views of a single-basket spline subassembly 109A/B/C shown bent at a radius R. The radius R may be variable. The spline subassembly 109A/B/C comprises a metallic spline core 109A, a core-supported flexible circuit 109B, and supported electrodes 109C. An electrically- and thermally-insulative over coating 111A (e.g., a conformal, dipped, or over-molded coating), is situated only in the non-ablating regions $L_1$ and $L_3$. Ablating region $L_2$ comprises the exposed spline core 109A and flexible electrode circuit 109B/C. Thus, in region $L_2$, heat can flow out of the tissue 106 across the thin flexible electrode circuit 109B/C and across the nitinol or other metallic spline core 109A. On the other hand, regions $L_1$ and $L_3$ are thermally insulated from blood and tissue by coating 111A. Thus, any heat which leaves tissue and tries to cross the spline subassembly 109A/B/C along thermally insulated regions $L_1$ and $L_3$ will be blocked. This arrangement creates a thermal compromise wherein the spline subassembly 109A/B/C allows thru-flow of heat where needed (i.e., in the ablating region $L_2$) and discourages heat from being extracted from non-ablating regions $L_1$ and $L_3$. An advantage of the design of this spline subassembly 109A/B/C is that a wide spline core 109A and a wide flexible electrode circuit 109B/C can be used, as localized heat flowing through the ablating spline region $L_2$ prevents a thermally untreated region from forming beneath the wide spline.

Figure 8B:
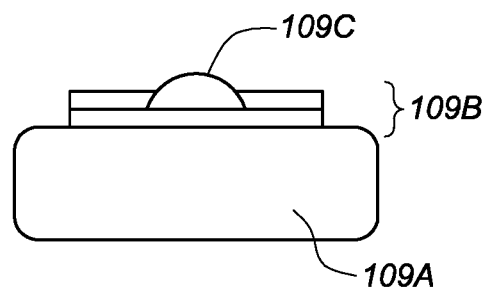
FIG. 8B is a schematic perspective view of a single-basket spline subassembly in accordance with the present disclosure.
Figure 8B:
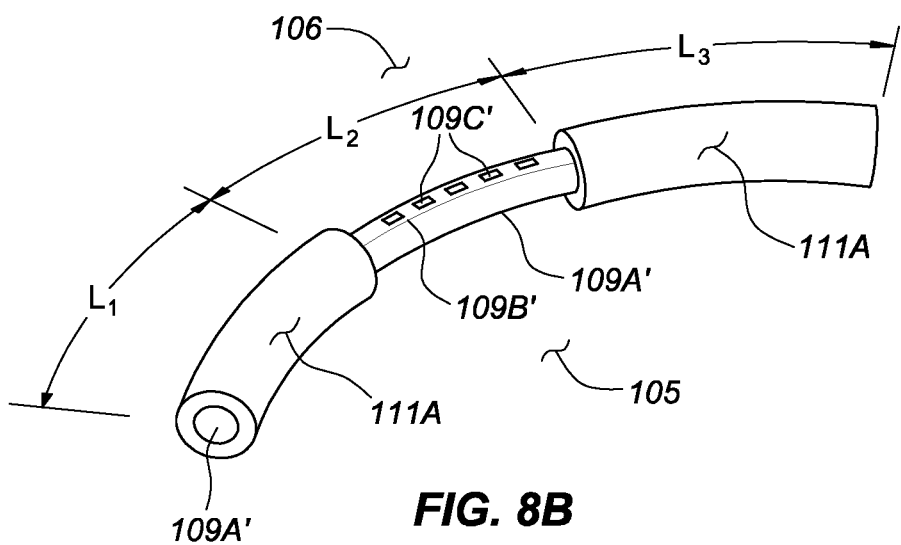

FIG. 8B is a schematic view of another embodiment of a single-basket spline subassembly 109A'/109B'/109C'. In this embodiment, the metallic spline core 109A' can be a round nitinol core. Similar to the embodiment shown in FIG. 8A, a thermally- and electrically-insulating material 111A coats the spline subassembly 109A'/109B'/109C' in regions $L_1$ and $L_3$. This arrangement creates a thermal compromise in which a lesion is formed underneath the spline in region $L_2$, but not in regions $L_1$ and $L_3$. The flexible circuit 109B' can comprise a circumferentially wrapped flexible circuit (not shown), a longitudinally bonded flexible circuit (as shown in FIG. 8B), or insulated wires wrapped around the spline core 109A' (not shown) and laser exposed at electrode sites 109C'.

It should be noted that the embodiments described above with respect to FIGS. 8A and 8B can be combined. For example, the spline core 109A/109A' can be rectangular in region $L_2$ and round in regions $L_1$ and $L_3$, or vice versa. It should further be noted that one or more of a thermocouple, thermistor or other temperature sensor in any of the sections $L_{1,2,3}$ and facing either toward tissue or toward the juxta-posed balloon, for example.

FIG. 8C is a schematic depiction of an embodiment of two adjacent splines 109A". The splines 109A" can be nitinol splines with a width $W_1$. Laminated to the splines 109A" are individual flexible circuits 109B". The flexible circuits 109B" are overhanging the physical edges of the splines 109A" in a region with a width $W_2$ that is wider than $W_1$. The splines can be rectangular, as shown, or round (as in FIG. 7b). The overhanging flexible circuits 109B" can be bonded (as shown) to the nitinol (or other spline material) splines 109A". Alternatively, the flexible circuits 9B" can be otherwise mechanically connected to the splines 109A", such as by surrounding them (not shown). In addition, the overhanging flexible circuits 109B" may overhang on one or both sides of each spline 109A". An advantage of a single-side overhang is that when the splines 109A" are collapsed they can more easily compress together along with their flexible circuits 109B". The overhanging flexible circuits 109B" are depicted as supporting electrodes 109C" as well as thermocouples 109D.

FIG. 8D is an isometric cross-sectional view through line Z-Z of FIG. 8C showing the overhanging flexible circuit 109B" and spline 109A". Phantom lines 112A and 112B show that the overhanging flexible circuit 109B" can be pre-formed and have a radius (not shown). The radius can make it easier for the splines 109A" and flexible circuits 109B" to close after being opened. Further, compression caused by a balloon, such as balloon 105 in FIGS. 2-6, could force the overhanging flexible circuits 109B" to be flattened or to conform against tissue and the inflated balloon surfaces.

Returning to FIG. 8C, the overhanging flexible circuits 109B" are depicted as laminated to the interior surfaces of the splines 109A" that face the backing balloon (not shown). Note, however, that the electrodes 109C" face the tissue 106 (shown in FIGS. 5A-C). Alternatively, the overhanging flexible circuits 109B" may be mounted on the exterior surfaces of the splines 109A" facing the tissue (not shown). In either case, the electrodes 109C" will face tissue and the thermocouples 109D may face tissue, the balloon, or a tissue/balloon interface. The thermocouples 109D may also be mounted in thru-holes in the overhanging flexible circuits 109B". Thus, by using flexible circuits, the electrical contact can be routed (during manufacture) to either flexible surface regardless of which surface faces the splines.

An advantage of having thermocouples 109D in the overhanging flexible circuits 109B" is that they can provide an accurate balloon/tissue interface temperature without being skewed by the thermal conductivity of an underlying or overlying heat-sinking spline. Another advantage of the overhanging flexible circuits 109B" is that the size of electrodes 109C" can be much larger than if they were laterally constrained to the spline width $W_1$ (as opposed to the wider $W_2$ dimension). The width $W_2$ of the overhanging flexible circuit portions 109B", shown in section Z-Z of FIG. 8D as potentially being pre-curved and balloon-flattened, might co-integrate a spring element or layer (not shown) to provide this springiness and positive radius in the proper direction of phantom lines 112A or 112B as selected during design. A third potential advantage of the overhanging flexible circuits 109B" is that they may allow for the use of fewer splines—such as three or four splines rather than five or six splines—at least in the case wherein the flexible circuits 109B" overhang splines 109A" on both sides. Using fewer splines allows more room for other elements.

FIG. 8C also shows, in phantom, a bridging flexible portion 113A connecting two overhanging flexible circuits 109B". At least part of the bridging flexible portion 113A may be pressed against tissue by the balloon 105 (see FIGS. 2-6). A bridging flexible electrode (and/or thermocouple) 113B, depicted in phantom, can be located on the bridging flexible portion 113A. Bridging flexible electrodes (and/or thermocouples) 113B can be present in addition to or instead of the spline-mounted electrodes 109C" or thermocouples 109D. Such bridged flexible circuitry can allow for fewer splines.

In an embodiment, a higher pressure balloon can be used to attain better thermal contact with tissue without mechanically overloading the ostium of the pulmonary vein. The higher pressure balloon may also allow for superior cryofreezing parameters, such as a faster cooling rate or more elastic deformation of the balloon into an asymmetrical ostium, particularly if the ostium is mechanically supported by splines. The present inventors believe that overexpansion of the balloon is less likely in a multi-spline arrangement because more elastic balloon deformation may be allowed than for a symmetric balloon with no splines. In other words, a more flexible balloon can bulge outward between splines without escaping from the spline structure.

A potential advantage to above-described embodiments, in which the splines 109A"/overhanging flexible circuits 109B" are not bonded directly to the balloon 105 (see FIGS. 2-6), is that the balloon 105 and overhanging flexible circuits 109B" may be less stressed and more reliable.

Figure 8E:
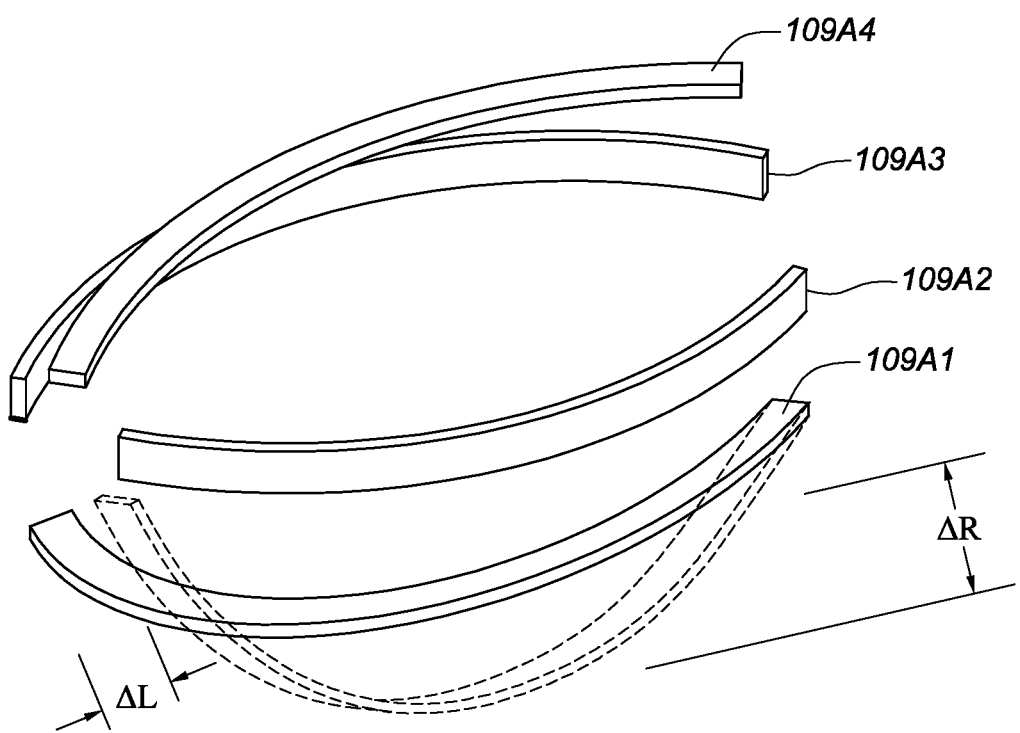
FIG. 8E is a schematic view of four splines in accordance with the present disclosure.

FIG. 8E is a schematic view showing four splines—109A1, 109A2, 109A3, and 109A4. Although four splines are shown here, any number of splines may be used. No flexible circuits, electrodes, or thermocouples are shown here for purposes of simplification. Each spline 109A1, 109A2, 109A3, 109A4 can be individually adjustable by an amount $\Delta L$, resulting in a radial position change of that specific spline by an amount $\Delta R$. The shape of the splines 109A1, 109A2, 109A3, 109A4 can be adjusted from round to oval to better seat electrodes and thermocouples in an oval-shaped pulmonary vein, such as at the superior left region of the of the heart. A mechanical mechanism, such as an axial sliding wire(s), can push or pull some or all of the splines 109A1, 109A2, 109A3, 109A4 in order to adjust their shape.

Figure 9A:
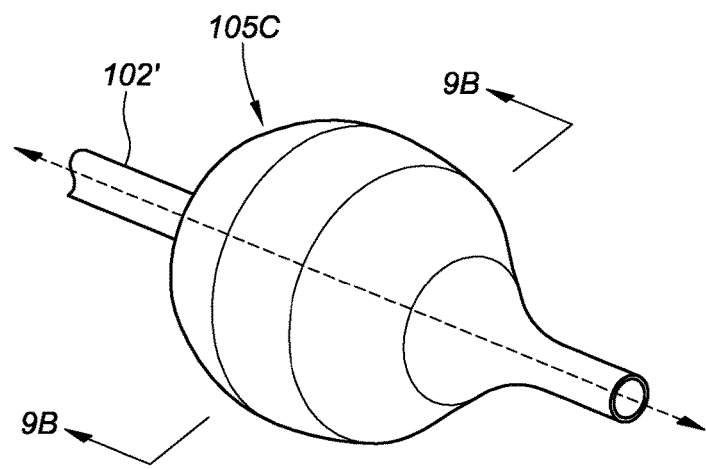
FIG. 9A is a schematic view of an embodiment of a balloon for use with a spline structure in accordance with the present disclosure.
Figure 9B:
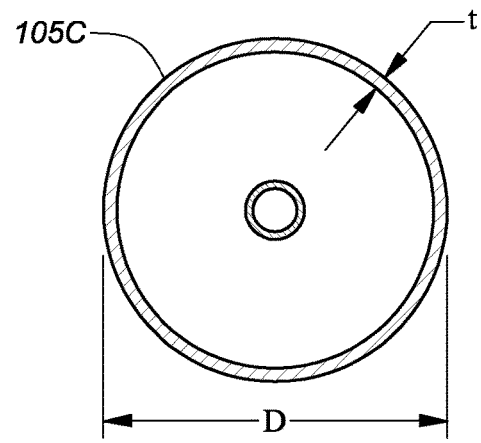
FIG. 9B is a cross-sectional view through line 9B-9B of FIG. 9A, in accordance with the present disclosure.
Figure 9C:
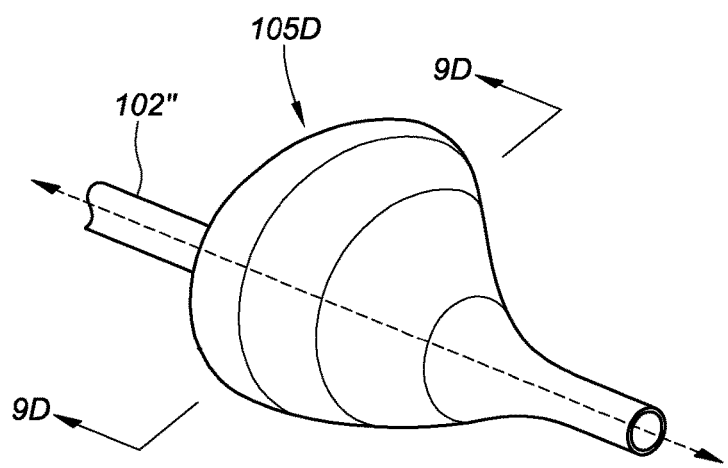
FIG. 9C is a schematic view of an embodiment of a balloon for use with a spline structure in accordance with the present disclosure.
Figure 9D:
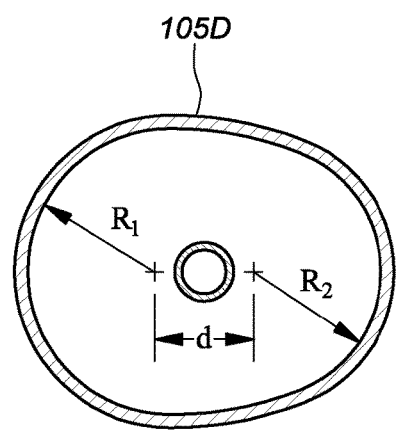
FIG. 9D is a cross-sectional view through line 9D-9D of FIG. 9C, in accordance with the present disclosure.

FIGS. 9A-9D are schematic views of various balloon embodiments that can be used in accordance with the present disclosure. In FIG. 9A, a symmetrical balloon 105C is depicted at a distal end of a delivery lumen 102'. As shown in FIG. 9B, the symmetrical balloon 105C has a diameter D and thickness t. In FIG. 9C, an asymmetrical balloon 105D is depicted at a distal end of a delivery lumen 102". As further shown in FIG. 9D, the asymmetrical balloon 105D has an elliptical or oval section defined by two radii, $R_1$ and $R_2$, which are separated by a distance d.

The asymmetrical balloon 105D may align with an asymmetric shape of a pulmonary vein ostium, thereby facilitating entry and sealing of the catheter balloon against tissue. The orientation or alignment of the balloon 105D can be determined in several ways. Radiographic markers (not shown) on the asymmetrical balloon 105D may be used in conjunction with fluoroscopy to indicate the orientation of the balloon 105D. Contrast injection may be used instead of or in addition to radiographic markers to determine the orientation of the balloon 105D. In addition, the splines 109A1, 109A2, 109A3, 109A4 shown in FIG. 8E may be employed in an asymmetrical shape and inserted into an asymmetrical pulmonary vein ostium, after which the asymmetrical balloon 105D (or even the symmetrical balloon 5C) can be inflated within the splines 109A1, 109A2, 109A3, 109A4.

Figure 10A:
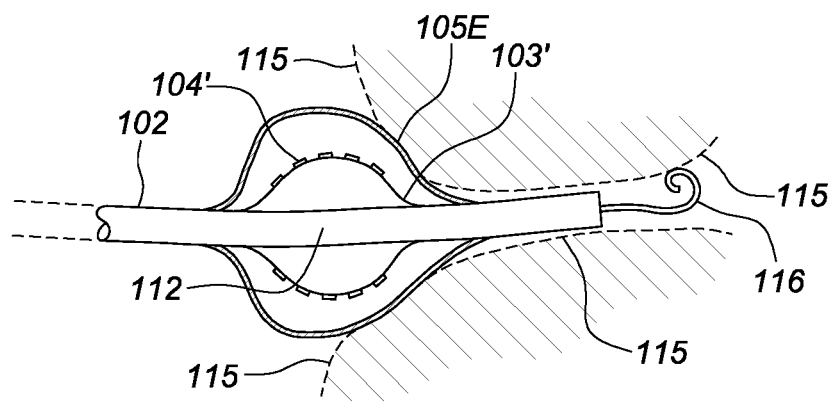
FIGS. 10A-D are schematic views depicting embodiments in which a balloon does not inflate associated splines, in accordance with the present disclosure.
Figure 10B:
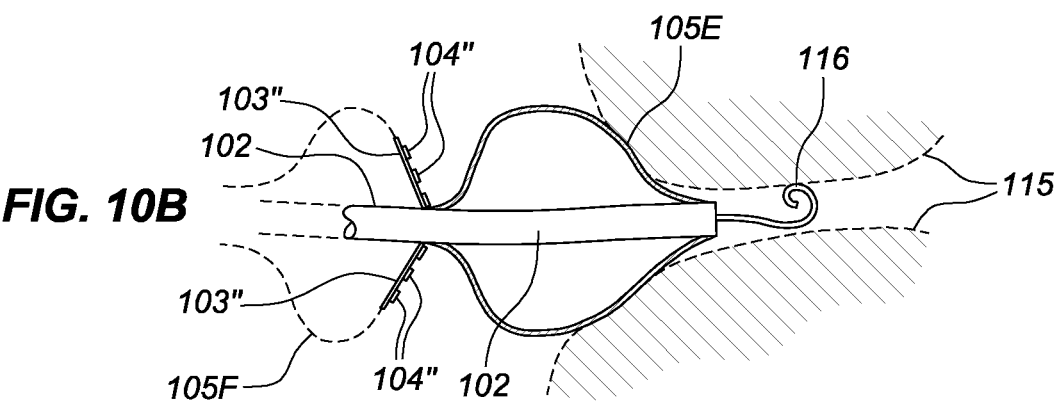

FIGS. 10A-10D are schematic views depicting another embodiment in which a balloon 105E (e.g., a cryoballoon) does not inflate associated splines 103'. In FIG. 10A, the balloon 105E contains a small EP basket comprised of splines 103' (which may comprise flexible circuits without a metal spline backer) and energy transfer elements 104'. This "standoff EP basket" electrically operates through the walls of the balloon 105E before, during, or after cryoablation. As shown in FIG. 10B, the splines 103' may be replaced by legs of a flexible circuit 103", forming an axial EP array of energy transfer elements 104" proximal the cryoballoon 105E. It may have its own activation balloon 105F, shown in phantom. The energy transfer elements 104" of FIG. 10B can be particularly good at picking up EP activity around the pulmonary vein ostium 115 around or under the balloon 105F on surfaces sloped toward the EP array. As depicted in FIGS. 10A-10D, element 116 represents a wire hook retainer.

Figure 10C:
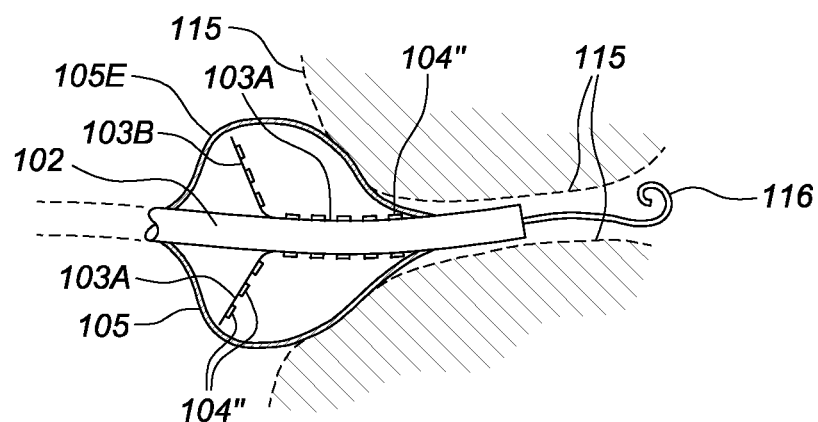
Figure 10D:
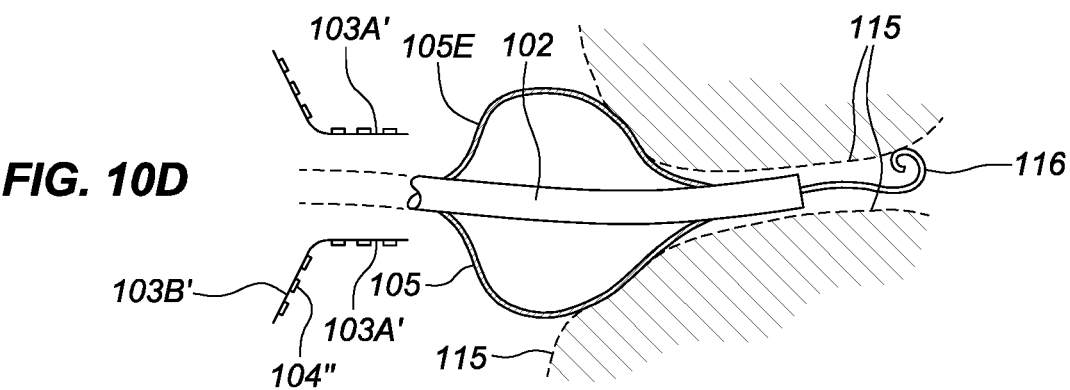

In FIG. 10C, an EP array (basket) has a radial looking axial part 103A and a forward-looking annular part 103B. Again, the radial part can 103A detect EP activity in the pulmonary vein lumen, whereas the annular part 103B can detect EP activity on the pulmonary vein ostium face 115. In FIG. 10D, a combination side-looking radial portion 103A' and forward-looking annular basket portion 103B' is shown. The EP mapping structures 103A' and 103B' can slide over the deflated balloon 105E, permitting both contact-free mapping (as shown, for example, in FIGS. 10A and 10C) and contact-mapping.

It should be appreciated that the balloon dielectric constant, conductivity, and thickness may need to be optimized for signal integrity according to the substance that fills the balloon (e.g., balloon 105E or 105F in FIG. 10B) during mapping. The balloon may be filled with cryovapor, cryoliquid (cryomedix), saline, or a gas such as $CO_2$.

It should also be appreciated that both a contact mapping array (as shown, for example, in FIGS. 6 and 7) and a non-contact mapping array (as shown, for example, in FIGS. 10A and 10C) can be combined in a single device. While contact mapping arrays generally provide the most accuracy, non-contact mapping arrays have the advantage of not needing to be flattened against tissue (i.e., "standing off" the tissue). Thus, a device that combines both contact and non-contact mapping arrays can provide advantages of each technique.

Although at least one embodiment of an apparatus and method for cooling tissue has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and can include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure can be made without departing from the spirit of the disclosure as defined in the appended claims.

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A catheter comprising:
   a catheter shaft having a proximal end portion and a distal end portion, the catheter shaft defining a fluid delivery lumen and an inflating lumen;
   a balloon configured to be coupled to the distal end portion of the catheter shaft, wherein the balloon defines a volume in fluid communication with the fluid delivery lumen and flow-coupled in-situ with the inflating lumen, wherein the balloon and the inflating lumen are partially positioned within the fluid delivery lumen; and
   a plurality of energy transfer elements disposed on top of a flexible circuit and along at least a portion of the balloon, wherein the plurality of energy transfer elements and the flexible circuit are disposed on top of a metal spline,
   wherein the balloon and the metal spline are separately expandable and/or collapsible.

2. The catheter of claim 1, wherein the plurality of energy transfer elements comprises at least one ablation electrode.

3. The catheter of claim 1, wherein the plurality of energy transfer elements comprises at least one of a sensing electrode, a flexible electrode, a mapping electrode, and a pacing electrode.

4. The catheter of claim 1, wherein the plurality of energy transfer elements are situated along an outer circumference of the balloon when the balloon is in an expanded state.

5. The catheter of claim 1, wherein the metal spline is configured to support the balloon and to be coupled to the distal end portion of the catheter shaft, wherein the metal spline comprises a plurality of individual splines.

6. The catheter of claim 5, wherein each spline is configured to support at least one of the plurality of energy transfer elements.

7. The catheter of claim 5, wherein each spline is configured to support at least one temperature sensor.

8. The catheter of claim 5, wherein each spline is configured to support the flexible circuit including at least one of the plurality of energy transfer elements and a temperature sensor, and wherein the balloon is configured to compress the flexible circuit toward a tissue.

9. The catheter of claim 8, wherein the temperature sensor is configured to detect a temperature at an interface between the balloon and the tissue.

10. The catheter of claim 8, wherein the flexible circuit is configured to overhang edges of the metal spline.

11. The catheter of claim 10, further comprising a bridging flexible portion configured to connect two overhanging flexible circuits.

12. The catheter of claim 1, wherein the balloon comprises at least one internal electrode.

13. The catheter of claim 1, wherein the balloon is a double balloon configured with an inner balloon and an outer balloon.

14. The catheter of claim 1, further comprising an over-coating disposed only in a non-ablation region of the plurality of energy transfer elements.

15. An ablation catheter assembly comprising:
a catheter shaft defining a fluid delivery lumen and an inflating lumen;
a balloon attached to the catheter shaft and the fluid delivery lumen, wherein the balloon is transformable between a delivery state and an expanded state, and wherein the balloon, in the expanded state, spans an area greater than a cross sectional area of the catheter shaft to which the balloon is attached, wherein the balloon and inflating lumen are partially positioned within the fluid delivery lumen; and
a plurality of ablation electrodes positioned on top of a flexible circuit and along an outer surface of the balloon when the balloon is in the expanded state, wherein the plurality of ablation electrodes and the flexible circuit are positioned on top of a metal spline,
wherein the balloon and the metal spline are separately expandable and/or collapsible.

16. The assembly of claim 15, further comprising at least one sensing electrode positioned along the outer surface of the balloon, when the balloon is in the expanded state.

17. The assembly of claim 15, wherein the metal spline is configured to support the balloon and to be coupled to a distal end portion of the catheter shaft, wherein the metal spline comprises a plurality of individual splines.

18. The assembly of claim 17, wherein each spline is configured to support at least one of the plurality of ablation electrodes.

19. The assembly of claim 17, wherein each spline is configured to support at least one temperature sensor.

20. The assembly of claim 17, wherein each spline is configured to support the flexible circuit including at least one of the plurality of ablation electrodes and a temperature sensor, and wherein the balloon is configured to compress the flexible circuit toward a tissue.

21. The assembly of claim 20, wherein the temperature sensor is configured to detect a temperature at an interface between the balloon and the tissue.

22. The assembly of claim 20, wherein the flexible circuit is configured to overhang edges of the metal spline.

23. The assembly of claim 22, further comprising a bridging flexible portion configured to connect two overhanging flexible circuits.

24. The assembly of claim 15, wherein the balloon is a double balloon configured with an inner balloon and an outer balloon.

25. The assembly of claim 15, further comprising an over-coating disposed only in a non-ablation region of the plurality of ablation electrodes.

* * * * *